United States Patent
Wachs

(10) Patent No.: US 6,875,724 B2
(45) Date of Patent: Apr. 5, 2005

(54) DUAL CATALYST BED REACTOR FOR METHANOL OXIDATION

(75) Inventor: Israel E. Wachs, Bridgewater, NJ (US)

(73) Assignee: Lehigh University, Bethlehem, PA (US)

( * ) Notice: Subject to any disclaimer, the term of this patent is extended or adjusted under 35 U.S.C. 154(b) by 201 days.

(21) Appl. No.: 10/387,546

(22) Filed: Mar. 14, 2003

(65) Prior Publication Data

US 2003/0176744 A1 Sep. 18, 2003

Related U.S. Application Data

(62) Division of application No. 09/950,832, filed on Sep. 13, 2001, now Pat. No. 6,559,345.
(60) Provisional application No. 60/232,426, filed on Sep. 14, 2000.

(51) Int. Cl.$^7$ .......................... B01J 23/22; B01J 23/28; B01J 21/06
(52) U.S. Cl. .................. 502/309; 502/305; 502/321; 502/353; 502/350; 422/188; 422/211
(58) Field of Search .................. 502/305, 321, 502/309, 353, 350; 422/188, 211

(56) References Cited

U.S. PATENT DOCUMENTS

| 2,065,394 A | 12/1936 | Punnett |
| 3,978,136 A | 8/1976 | Friedrich et al. |
| 4,343,954 A | 8/1982 | Hoene |
| 4,421,938 A | 12/1983 | Windawi |
| 5,118,868 A | 6/1992 | Sarup et al. |
| 5,217,936 A | 6/1993 | Sarup et al. |
| 6,245,708 B1 | 6/2001 | Wachs et al. |
| 6,559,345 B2 * | 5/2003 | Wachs ................ 568/471 |
| 2003/0171624 A1 * | 9/2003 | Wachs et al. ............ 568/487 |

FOREIGN PATENT DOCUMENTS

| EP | 0 199 359 | 10/1986 |
| GB | 1 463 174 | 2/1977 |
| WO | WO 98/23360 | 6/1998 |
| WO | WO 99/52629 | 10/1999 |
| WO | WO 99/52630 | 10/1999 |

OTHER PUBLICATIONS

EPO International Search Report from related application PCT/US 01/28341, dated Jun. 3, 2002.
EPO International Search Report from related application PCT/US 01/28353, dated Jun. 7, 2002.
Jehng et al. *Applied Catalysis A*, 83, 179–200 (1992).
Jehng and Wachs, *Catalysis Today*, 16, 417–426, (1993).
Kim and Wachs, *Journal Catalysis*, 141, 419–429, (1993).
Deo et al. *Journal Catalysis*, 146, 335–345, (1994).
Jehng et al. *J. Chem. Soc. Faraday Trans*, 91(5), 953–961, (1995).
Kim et al. *Journal of Catalysis*, 146, 268–277, (1994).
Banares et al., *Journal of Catalysis*, 150, 407–420, (1994).
Jehng and Wachs, *Catalyst Letters*, 13, 9–20, (1992).
G. Deo and I. Wachs, *Journal of Catalysis*, 146, 323–334 (1994).
G. Deo and I. Wachs *Journal of Catalysis* 146, 335–345 (1994).

* cited by examiner

Primary Examiner—Christina Johnson
(74) Attorney, Agent, or Firm—Banner & Witcoff, Ltd.

(57) ABSTRACT

A process and apparatus for oxidizing methanol in a gas stream into formaldehyde in a fixed bed reactor. The process first introduces a gas stream into a fixed bed reactor. The fixed bed reactor contains a catalyst bed having a depth, a width, a length, an inlet, an upstream region, a downstream region and an outlet. Preferably, the inlet, the upstream region, the downstream region and the outlet are provided in the order stated. A vanadia-titania catalyst is provided in the upstream region and a molybdena-titania catalyst is provided in the downstream region. The vanadia-titania catalyst in the upstream region is substantially free of $MoO_3$ and initially (i.e., during oxidation some $V_2O_5$ may sublime and migrate to the downstream region) the molybdena-titania catalyst in the downstream region is substantially free of $V_2O_5$. Next, the gas stream is contacted with the vanadia-titania catalyst under oxidizing conditions. Then, the gas stream is contacted with a molybdena-titania catalyst under oxidizing conditions which provides a product stream containing formaldehyde at the desired conversion and formaldehyde selectivity.

5 Claims, 1 Drawing Sheet

DUAL CATALYST BED REACTOR FOR METHANOL OXIDATION

This application is a divisional application of prior filed U.S. application Ser. No. 09/950,832, filed Sep. 13, 2001 now U.S. Pat. No. 6,559,345, which claims the benefits of provisional application 60/232,426, filed Sep. 14, 2000.

FIELD OF THE INVENTION

The invention relates to a process for oxidizing methanol or methanol-containing waste streams. More particularly, this invention is directed to a method for oxidizing methanol in a gas stream (for example, pure methanol or a paper pulp mill waste stream of methanol, methyl mercaptan and other waste products) to form formaldehyde ($CH_2O$) by passing the gas stream through a catalyst bed containing, in a specified distribution, at least two metal oxide supported catalysts.

BACKGROUND OF THE INVENTION

A method for converting methanol in a methanol gas stream or in a waste gas stream to formaldehyde involves contacting the gas stream with any one of a variety of supported metal oxide catalysts under oxidizing conditions. The constituents of the gas stream can be fully or partially oxidized. However, partial oxidation of methanol to formaldehyde is preferred.

Vanadia-titania ($V_2O_5$ supported on $TiO_2$) and molybdena-titania ($MoO_3$ supported on $TiO_2$) supported catalysts are two catalysts developed for selectively oxidizing methanol to formaldehyde. Both of these catalysts are highly active. The vanadia-titania catalyst is the more active of the two.

Unfortunately, both of these catalysts have disadvantages associated with their use. For example, vanadia-titania catalysts exhibit a high catalytic activity. Accordingly, such catalysts oxidize methanol to formaldehyde and continue to further oxidize the formaldehyde into undesirable oxidation products including carbon monoxide (especially when a high concentration of formaldehyde is available). Consequently, formaldehyde yield is undesirably lowered.

One of the disadvantages associated with molybdena-titania catalysts is due to the volatility of molybdenum trioxide (or other volatile Mo species) contained therein. In particular, the oxidation of methanol to formaldehyde is highly exothermic. The exothermic nature of the oxidation reaction in combination with the high catalytic activity of the molybdena-titania catalyst (and/or the high catalytic activity of other catalysts used in combination with molybdena-titania catalysts) creates hot spots on the catalyst surface during methanol oxidation to formaldehyde. As more methanol is oxidized, the temperature at these hot spots continues to increase. Finally, these hot spots reach a temperature sufficient to sublime molybdenum trioxide (or other volatile Mo species present in the catalyst).

When molybdena-titania catalysts are distributed in an upstream region of a catalyst bed, molybdenum trioxide (or other volatile Mo species) tends to migrate to the cooler downstream regions of the catalyst bed where it condenses into crystalline structures, such as needles. Ultimately, accumulation of these crystalline structures in the downstream regions of the catalyst bed impede the flow of the incoming feed stream (containing methanol) being introduced into the catalyst bed. Thereby, methanol oxidation and catalytic activity are undesirably suppressed.

For $MoO_3$ catalysts having less than monolayer coverage on $TiO_2$, the aforementioned $Mo/MoO_3$ volatility and sublimation may not be problematic. However, for $MoO_3$ catalysts with greater than monolayer coverage on $TiO_2$ or the like, $Mo/MoO_3$ volatility and sublimation is typically problematic. Nevertheless, $MoO_3/TiO_2$ catalysts offer some advantages (e.g., over vanadia-titania catalysts) including their lower activities for oxidizing formaldehyde. Accordingly, formation of further oxidation products of formaldehyde (e.g., CO, $CO_2$, and the like) may be avoided or attenuated by using $MoO_3/TiO_2$ catalysts rather than, for example, using $V_2O_5/TiO_2$ catalysts.

Even with their associated disadvantages, there have been numerous attempts to use these catalysts (e.g., vanadia-titania and molybdena-titania sometimes in combination with other catalysts) to achieve a high conversion of methanol together with a high selectivity for formaldehyde. Freidrich et al., U.S. Pat. No. 3,978,136, discloses a combination of $MoO_3$ and ferric oxide ($Fe_2O_3$) on a sole titania support where the molar ratio of Mo:Fe is less than 10:1. This catalyst exhibits conversions of approximately 99% with a selectivity of approximately 92% at a reactor temperature of approximately 290° C. However, this catalyst system suffers from the aforementioned molybdenum trioxide volatility problem. Hoene, U.S. Pat. No. 4,343,954, discloses a sequential two catalyst, two reactor system using a silver catalyst (in a first reactor) and a metal oxide catalyst selected from a group including vanadium and molybdenum (in a second reactor). However, the use of the silver catalyst requires an extremely high temperature (approximately 600° C.) and a subsequent cooling step between the two reactors. As such, silver catalyst systems are prohibitively expensive to use. Windawi, U.S. Pat. No. 4,421,938, discloses a combination of $MoO_3$ and any of a list of other metal oxides (not including vanadium) on the same alumina/inorganic oxide support. Sarup et al., U.S. Pat. No. 5,118,868 and U.S. Pat. No. 5,217,936, discloses a catalyst comprised of mixed oxides of molybdenum and another metal oxide (M), including vanadium, with a molar ratio of Mo:M from 1:1–5:1, where the mixed oxides are supported on corrugated sheets of fibrous material. However, none of these approaches adequately solve or address the volatility problem associated with the use of $MoO_3$ or the undesirable oxidation of formaldehyde to its further oxidation products associated with the use of $V_2O_5$.

SUMMARY OF THE INVENTION

It is therefore an object of the present invention to provide a method for the partial oxidation of methanol or methanol-containing waste gas streams to formaldehyde by passing the gas stream and an oxidizing agent, at oxidizing conditions, over a catalyst bed of two or more catalysts distributed in a manner which substantially alleviates and/or eliminates the aforementioned undesirable further oxidation of formaldehyde (e.g., carbon monoxide formation or other formaldehyde oxidation products) and molybdenum trioxide volatility problems (e.g., the formation of crystalline needles in the downstream region).

It has surprisingly been discovered, for example, that the use of vanadia-titania catalysts positioned upstream in the catalyst bed of a fixed bed reactor (upstream regions being the regions closer to the reactor's entrance) combined with molybdena-titania catalysts positioned further downstream in the reactor's catalyst bed yields a methanol conversion greater than 99% while substantially eliminating the undesirable further oxidation of formaldehyde to carbon monoxide (or other formaldehyde oxidation products) together with substantially avoiding the aforementioned $MoO_3$ volatility problems.

DETAILED DESCRIPTION OF THE PREFERRED EMBODIMENTS

Figure 1:
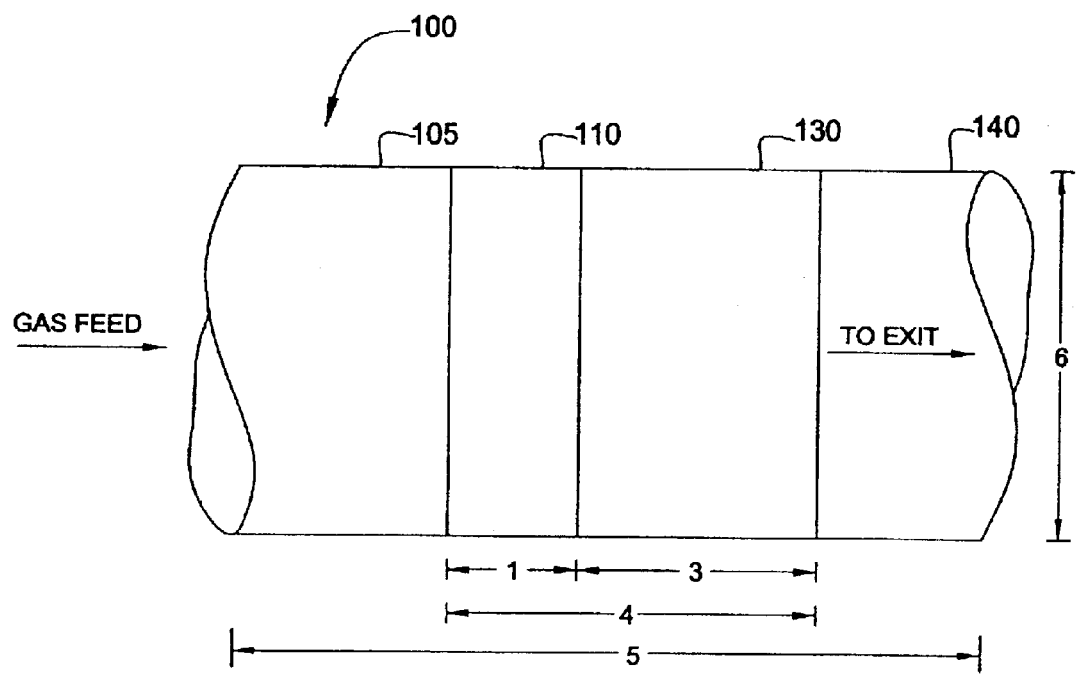
FIG. 1 is a schematic of an exemplary tubular fixed bed reactor.

Applicant's invention relates to a means and a method for oxidizing gas phase methanol, methanol-containing waste streams (e.g., pulp mill waste streams commonly known as Stripper Overhead Gas-SOG) and the like. Preferably, according to the invention, the methanol gas stream, in combination with an oxidizing agent and an inert carrier gas are passed, at oxidizing conditions, through a fixed bed reactor containing a catalyst bed that is comprised of at least two supported metal oxide catalysts distributed in a manner as to achieve high selectivities and high conversions of methanol to formaldehyde. For example, a vanadia-titania catalyst is distributed in the upstream region of a catalyst bed and the molybdena-titania catalyst is distributed in the downstream region of a catalyst bed. When the feed stream is pure gas-phase methanol combined with an oxidizing agent (e.g., $O_2$, air, etc.) and an inert carrier gas (e.g., $N_2$, He, Ar, mixtures thereof, etc.), the oxidation reactions carried out over this catalyst bed of a fixed-bed reactor can readily achieve, for example, a conversion of approximately 99% and a high selectivity (e.g., 70%–80%) for the formation of formaldehyde As used herein, the term "methanol" is intended to include pure methanol streams, paper (pulp) mill waste gas streams containing methanol, other waste gas streams containing methanol, methyl mercaptan and/or mixtures thereof.

As used herein, the term "selectivity" is determined by dividing the number of moles of formaldehyde formed by the number of moles of methanol consumed (from the feed stream to the reactor) times 100. Accordingly, selectivity is a percentage value. Selectivity indicates the percentage of formaldehyde formed as compared to the percentage of non-formaldehyde oxidation products of methanol, such as, carbon monoxide, carbon dioxide, etc.

As used herein, the term "conversion" is determined by dividing the difference between the number of moles of methanol fed to the reactor minus the number of moles of methanol exiting the reactor by the total number of moles of methanol fed to the reactor times 100. Accordingly, conversion is a percentage value. Conversion indicates the percentage of the moles of methanol that were oxidized to formaldehyde and any other non-formaldehyde oxidation products of methanol. Thus, if 2 moles of methanol are fed into the reactor yielding 1 mole of formaldehyde and 1 mole of methanol, then selectivity would equal 100% while conversion would equal 50%.

The vanadia-titania catalyst suitable for use with this invention can be any of the known vanadia-titania catalysts with the proviso that the vanadia-titania catalyst is essentially free of $MoO_3$ (or any other volatile Mo species prone to sublimation at hot spots) in an amount sufficient to substantially impede the flow of methanol due to the aforementioned Mo/$MoO_3$ volatility problem. Preferably, the vanadia-titania catalyst, distributed in the upstream region, is free of $MoO_3$ and/or other similar volatile metallic oxides that poison the catalyst bed. For example, the amount of $MoO_3$ should be no more than (a) 0.1%–3% (e.g., 1%) by weight based on the total weight of the vanadia-titania catalyst including any catalyst support or any other inert (or non-inert) material or (b) the moles of $V_2O_5$ of the vanadia-titania catalyst. Preferably, the vanadia-titania catalysts suitable for use in conjunction with this invention include, but are not limited to available vanadia-titania catalysts where the vanadia content is less than or equal to an amount sufficient to form a monolayer on the titania. Without being bound by any theory, because it is believed that $V_2O_5$ is volatile at oxidation conditions when the vanadia content is greater than an amount sufficient to form a monolayer on the $TiO_2$, a monolayer or less content of vanadia is preferred The molybdena-titania catalyst suitable for use with this invention can be any one of the known molybdena-titania catalysts with the proviso that fresh molybdena-titania catalyst is essentially free of $V_2O_5$ (or any other similar species) in an amount sufficient to substantially oxidize formaldehyde into carbon monoxide and/or other non-formaldehyde oxidation products. Preferably, the molybdena-titania catalyst is initially free of $V_2O_5$ and/or other similar metal oxides that are highly active and which undesirably oxidize formaldehyde to carbon monoxide and/or other non-formaldehyde oxidation products. However, for example, as methanol oxidation proceeds, some $V_2O_5$ may sublime and migrate from an upstream region of the catalyst bed into the molybdena-titania catalyst distributed in a downstream region of the catalyst bed. Molybdena-titania catalysts suitable for use in conjunction with this invention include, but are not limited to commercially known molybdena-titania catalysts.

Preferably, the vanadia and the molybdena are primarily provided as a metal oxide overlayer (e.g., a two-dimensional overlayer) having a noncrystalline form, respectively. An exemplary support useful in the process of this invention generally comprises a metal oxide substrate, such as titania ($TiO_2$). The surface of the substrate is typically modified with a layer of an oxide of vanadium or an oxide of molybdenum (e.g., deposited as a metal oxide overlayer). The supported catalysts (e.g., $V_2O_5$ on $TiO_2$ or $MoO_3$ on $TiO_2$) behave differently than the unsupported bulk oxides (e.g., $V_2O_5$ or $MoO_3$). Preferably, the metal oxide (e.g., $V_2O_5$ or $MoO_3$) overlaid on the substrate should be provided in an amount sufficient to attach to the substrate surface without exhibiting properties of the bulk metal oxide (e.g., unsupported $V_2O_5$ or unsupported $MoO_3$).

Preferably, at least about 25 wt. % of the metal oxide coating (e.g., $V_2O_5$ or $MoO_3$) will be in a noncrystalline form. Typically, if the metal oxide loading on the titania support broadly ranges from about 0.1 wt % to about 35 wt. % of the total catalyst weight (including the weight of the support substrate) then at least 25 wt. % will be in non-crystalline form. Further, for example, titania may be employed in its anatase and/or rutile forms. For example, at least about 25 wt. % (and generally from about 50 wt. % to about 100 wt. %) of the titania may be in the anatase form. The above-noted wt. % values are based on the total weight of the catalyst including the weight of the support substrate. As recognized by those skilled in the art, the titania support material should be sufficiently free of impurities to prevent interference with the desired oxidizing catalytic activity (i.e., catalyzing the oxidation of methanol to formaldehyde to provide the desired conversion and selectivity for formaldehyde). The titania may be prepared by any known conventional technique.

For example, the metal oxide supported catalysts of this invention may be prepared by impregnation techniques well-known in the art, such as incipient wetness, grafting, equilibrium adsorption, vapor deposition, thermal spreading, and the like. When using an incipient wetness impregnation technique, an aqueous or nonaqueous (e.g., organic) solution containing a metal oxide precursor compound (e.g., a precursor of $V_2O_5$ or a precursor of $MoO_3$ together with an appropriate solvent thereof) is contacted with titania. The metal oxide precursor (such as a salt) solution used may be aqueous or organic, with an amount of solvent sufficient to dissolve the precursor. Over time the metal oxide precursor material is deposited onto the substrate support, for example, by selective adsorption. Any excess solvent may be evaporated leaving behind the metal oxide precursor or its salt. Other impregnation techniques, such as vapor deposition and thermal spreading, do not require use of a solvent as does incipient wetness. These techniques may be desirable in some circumstances where, for example, volatile organic carbon (VOC) emissions are problematic. Alternatively, a suspension containing metal oxide particles (e.g., particles of $V_2O_5$ or particles of $MoO_3$) may be used to spread the metal oxide particles on the substrate following the evaporation of the suspending vehicle at a temperature from about 100° C. to about 200° C. and calcination of the substrate and metal oxide particles at a temperature from about 400° C. to about 600° C. Further, the titania used in the catalyst of this invention may be composed of substantially porous particles of a diameter from about 0.4 to about 0.7 micron. Preferably the titania support has a specific surface area of at least about 1 $m^2/g$ (e.g., 9.5 $m^2/g$).

One way to disperse vanadium oxide onto a titania support is to impregnate exemplary titania spheres or powders with a solution containing a vanadium compound. For example, when impregnating a substrate, the vanadium is introduced, preferably dissolved in an aqueous solution, followed by drying and calcining. Criteria used to select the vanadium compounds include whether the compounds are soluble in the desired solvent and whether the compounds decompose at an acceptable rate at the calcination temperature to give the appropriate activated metal oxide. (e.g., $V_2O_5$ or $MoO_3$). Illustrative of suitable compounds of vanadium for use in conjunction with this invention include, but are not limited to, vanadium halides, vanadium oxyacids, vanadium oxyacid salts, vanadium oxysalts, and/or other vanadium salts. Specific examples include vanadium tribromide, vanadium dichloride, vanadium trichloride, vanadium oxychloride, vanadium oxydichloride, vanadic acid, vanadyl sulfate, vanadium alkoxides, vanadium oxalate (which may be formed in situ by reaction of $V_2O_5$ with an aqueous solution of oxalic acid), and ammonium meta-vanadate.

Suitable metal oxide precursor compounds for making the molybdena-titania catalysts used in conjunction with this invention include but are not limited to ammonium heptamolybdate, molybdenum oxalate, molybdenum halides, molybdenum alkoxides, or mixtures thereof. Other suitable molybdena-titania catalysts are well known to those of ordinary skill in the catalysis art. The impregnation of the exemplary titania support (e.g., spheres, powders, or other shapes) with the metal oxide precursor compound solution may be carried out, as noted above, in ways well known in the art using either wet or dry impregnation techniques. One convenient method is to place the titania particles into a rotary evaporator which is equipped with a steam jacket. An impregnating solution of a precursor compound which contains an amount of the desired metal (e.g., V or Mo) to be included in the finished catalyst (as the metal) is added to the support particles and the mixture is cold rolled (no steam) for a time from about 10 to about 60 minutes. The cold rolling time should be sufficient to impregnate the support with the precursor compound solution. Water-soluble precursor compounds are generally preferred for industrial applications because of environmental concerns regarding VOC emissions. Nonetheless, when using an organic solvent, initial heating may be conducted in a nitrogen atmosphere to remove any flammable solvent. Next, steam is introduced and the remaining solvent is evaporated. This usually takes from about 1 to about 4 hours. The impregnated support will normally be dried at temperatures ranging from about 50° C. to about 300° C. yielding a support with a metal-oxide precursor (e.g., precursor of $MoO_3$) overlayer thereon.

Eventually, the titania with the metal oxide precursor overlayer (e.g., precursor of $V_2O_5$ or precursor of $MoO_3$) thereon is removed from the rotary evaporator and calcined. The evaporation and calcination is conducted in a suitable oxidizing atmosphere such as air, other oxygen source gasses, etc. at a temperature typically from about 150° to about 800° C., and more preferably from about 400° to about 600° C. for about 1 to about 3 hours, respectively. The calcining is carried out over a period of time sufficient to convert the precursor compound on the titania to the corresponding metal oxide overlayer (e.g., $V_2O_5$ overlayer or $MoO_3$ overlayer). As recognized by those skilled in the art, calcining conditions need to be adjusted to avoid undesirably reducing the catalyst surface area or transforming the titania via solid state reactions. As is recognized by those skilled in the art, because some precursor compounds are air/moisture sensitive, they are prepared under nitrogen or other inert gas. Calcination time will, of course, depend on the temperature and, in general, may broadly range from about 0.5 to about 16 hours, though calcination times of less than about 7 hours may often be suitable. For example, calcination at about 450° C. for about 2 hours has proven to be suitable for adsorbing 1 wt. % (based on the final total catalyst weight) vanadia on the titania support. The precise time and temperature for calcination depends on the particular metal oxide overlayer used and should be selected to avoid substantial crystal phase transformation of the preferred titanium anatase form into another crystalline form, such as rutile. The anatase form is preferred to the rutile form because the former exhibits greater surface area than the latter. As such, the former form exhibits greater catalytic activity in comparison to that of the latter rutile form.

The supported catalysts of this invention will typically have surface metal oxide loadings (e.g., $V_2O_5$ or $MoO_3$) from about 0.1 wt. % to about 35 wt. % (based on the total active catalyst weight), preferably from about 1 wt. % to about 20 wt. %, more preferably from about 1 wt. % to about 15 wt. %, and even more preferably from about 1 wt. % to about 10 wt. %.

Additional details relating to the preparation and structure of overlayer metal oxide supported catalysts suitable for use in conjunction with the invention are well-known. For example, see Jehng et al., *Applied Catalysis A*, 83, 179–200, (1992); Jehng and Wachs, *Catalysis Today*, 16, 417–426, (1993); Kim and Wachs, *Journal of Catalysis*, 141, 419–429, (1993); Deo et al., *Applied Catalysis A*, 91, 27–42, (1992); Deo and Wachs, *Journal of Catalysis*, 146, 323–334, (1994); Deo and Wachs, *Journal of Catalysis*, 146, 335–345, (1994); Jehng et al., *J. Chem. Soc. Faraday Trans.*, 91(5), 953–961, (1995); Kim et al., *Journal of Catalysis*, 146, 268–277, (1994); Banares et al., *Journal of Catalysis*, 150, 407–420, (1994) and Jehng and Wachs, *Catalyst Letters*, 13, 9–20, (1992).

Typically, the titania support used in accordance with the invention has a surface area ranging from about 1 $m^2/g$ to about 150 m²/g or more (e.g., 5–10 m²/g). The titania may be used in any configuration, shape or size which exposes its surface and any metal oxide overlayer disposed thereon to come in contact with the gaseous stream containing methanol passed through the catalyst bed.

For example, titania can be employed in a particulate form or a deposited form. The deposited form includes, for example, titania (or vanadia on titania or molybdena on titania, etc.) deposited on a monolithic carrier or on ceramic rings or pellets or the like. Typically, a vanadia on titania catalyst is deposited on a ceramic or refractory inorganic carrier such as silicon carbide, silicon nitride, carborundum, steatite, alumina and the like. Rings or pellets are preferred. As particles, the titania, can be formed into various shapes, including but not limited to, pills, pellets, granules, rings, spheres, combinations thereof and the like. Alternatively, use of free particulates (e.g., unshaped titania) may be desirable when large catalyst volumes are needed and/or if the catalyst bed is operated in a fluidized state. Additionally, the active catalyst (e.g., $V_2O_5$ on $TiO_2$ or $MoO_3$ on $TiO_2$) will be applied to the inert ceramic support in an amount sufficient to provide, for example, from about 1 wt. % to about 20 wt. % by weight, and preferably from about 5 wt. % to about 15 wt. %, based on the total weight of the catalyst including the support substrate and any carrier thereof.

Figure 2:
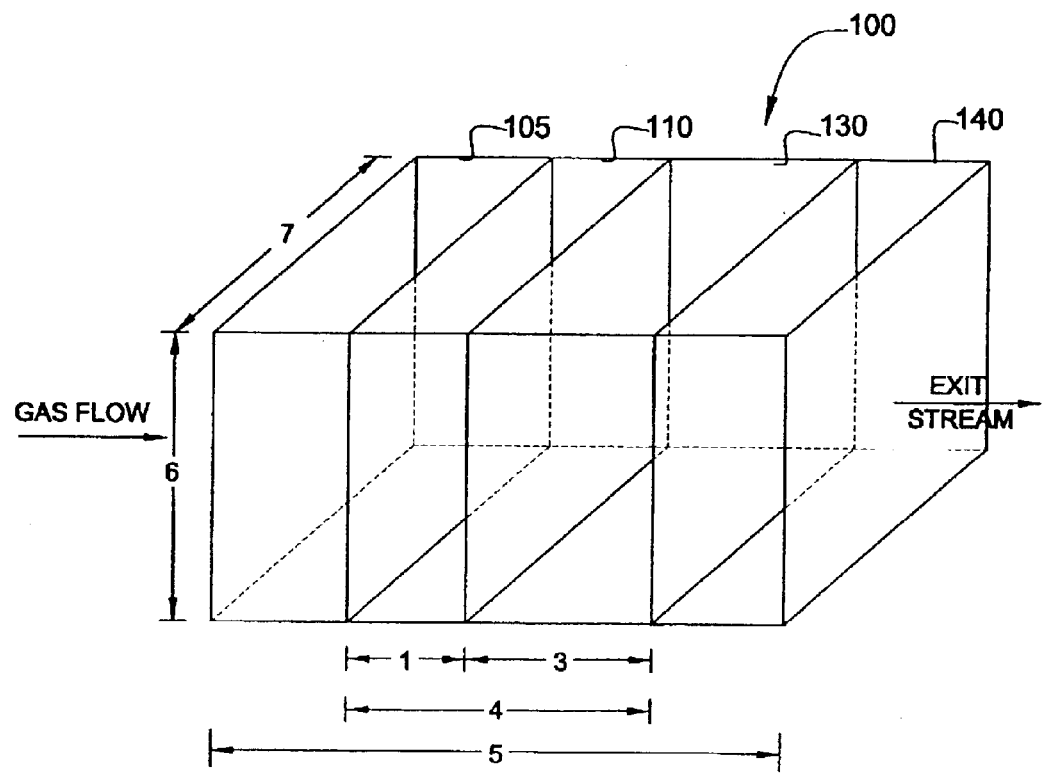
FIG. 2 is a schematic of an exemplary block-shaped fixed bed reactor.

As seen in FIGS. 1 and 2, an exemplary tubular fixed bed reactor (100) and an exemplary block fixed bed reactor (100) are depicted. Both have an entrance region (105), an upstream catalyst bed region (110) of depth (1), a downstream catalyst bed region (130) of depth (3), an exit region (140), a total catalyst bed depth (4), a total reactor length (5), and a reactor diameter (6), or a reactor width (7).

The distribution of the two aforementioned catalysts (e.g., $V_2O_5$ supported on $TiO_2$ and $MoO_3$ supported by $TiO_2$) is provided such that the highly active and selective vanadia-titania catalyst is distributed in an upstream (hot spot) region of the catalyst bed and the molybdena-titania catalyst is distributed downstream (in a region where hot spots are less frequent or essentially absent) of the vanadia-titania catalyst in the catalyst bed. A preferred catalyst distribution includes: (1) distributing the vanadia-titania catalyst in about the first fourth to about the first half (e.g., in about the first third to about the first half) of the catalyst bed depth nearest the reactor's entrance, and (2) distributing the molybdena-titania catalyst further downstream in the remaining about three-fourths to about one-half (e.g., about the remaining two-thirds to about one-half) of the depth of the catalyst bed. A particularly preferred catalyst distribution includes distributing the vanadia-titania catalyst in about the first third of the catalyst bed depth (nearest the reactor's entrance) and distributing the molybdena-titania catalyst further downstream in about the remaining two-thirds of the catalyst bed depth.

Methanol gas streams are transported to the reactor in a flowing stream of gas containing the methanol gas stream, oxygen and a carrier gas, such as He, $N_2$, Ar, or other inert gasses well known to those of ordinary skill. It is understood that the carrier gas is any of one or more gases that do not interfere with the operation of the invention. Accordingly, the carrier gas is at least substantially inert with respect to the methanol gas stream, the catalysts used, and the formaldehyde product. Preferably, gas streams have a mole ratio of methanol/oxygen from about 1:1 to about 1:4 and a mole ratio of methanol/inert carrier from about 1:12 to about 1:20. A preferred gas stream contains about 6 moles of methanol gas for about 16 moles of oxygen and for about 80 moles of helium, respectively. Additionally, suitable methanol gas stream oxidation conditions include a reactor temperature range from about 250° C. to about 400° C. A preferred reactor temperature is approximately 360° C.

To achieve high selectivity in the conversion of methanol to formaldehyde, it is important to sustain a flow rate (of the methanol gas stream to provide an amount of methanol per unit mass total of each individual catalyst) in the range from about $10^{-2}$ to about $10^5$ cubic centimeters of methanol (at standard temperature and pressure) per gram of active catalyst per minute (i.e., excluding the weight of the inert catalyst support material or any carrier material such as ceramic rings etc.). Given the typical composition of pulp mill waste gas, such conditions will also facilitate oxidation of other components in the gas stream. Generally, higher reaction temperatures permit higher flow rates. Usually, the process can be operated from about 0.1 to about $10^4$, standard cubic centimeters (sccm) of methanol per minute per gram of total active catalyst.

Typically, the flow rate (e.g., in terms of space velocity= ((sccm of gas flow)/(cc of catalyst volume)×(1 min/60 sec))) of the reactant gas feed stream fed into the inlet end of an exemplary fixed bed reactor ranges from about 0.1 sec$^{-1}$ to about 3.0 sec$^{-1}$, preferably form about 0.3 sec$^{-1}$ to about 2.5 sec$^{-1}$, more preferably from about 0.4 sec$^{-1}$ to about 2.2 sec$^{-1}$ and even more preferably from about 0.5 sec$^{-1}$ to about 1.5 sec$^{-1}$ The above noted catalytic distribution scheme substantially eliminates and/or reduces the aforementioned problems associated with each catalyst (e.g., vanadia-titania and molybdena-titania). In a preferred distribution, the vanadia-titania catalyst converts a large percentage of the methanol to formaldehyde in the first third of the bed depth. Limiting the vanadia-titania catalyst distribution to about the first third of the bed depth reduces prolonged contact between the vanadia-titania catalyst and the formaldehyde product (e.g., in high concentrations of formaldehyde). Thus, subsequent oxidation of the formaldehyde to undesirable oxidation products including carbon monoxide is minimized. The positioning of the molybdena-titania catalyst downstream of the vanadia-titania catalyst allows any residual methanol to be oxidized to formaldehyde. Because only limited quantities of residual methanol are present in the downstream region, hot spot formation is largely absent. With minimal hot spot formation (or an absence of hot spot formation), the problems associated with the volatility/sublimation of Mo/MoO$_3$ are substantially or altogether eliminated Further, since the molybdena-titania catalyst is a less active oxidizer than the vanadia-titania catalyst, prolonged contact between the high concentrations of formaldehyde and the molybdena-titania catalyst typically does not result in any substantial oxidation of formaldehyde to undesirable oxidation products including carbon monoxide.

As will be recognized by those skilled in the art, the gases exiting the reactor via the outlet end typically contain at least one or more of unreacted staring materials, inert gases, formaldehyde and/or water. Formaldehyde is the desirable oxidation product and it can be recovered from the gases exiting the reactor using any one of a number of ways known to those skilled in the art. Alternatively, it may be possible to utilize the gas stream (containing formaldehyde) as it exits the reactor bed without further purification.

The gases leaving the catalytic reactor are typically subject to further processing in a conventional manner. For example, the formaldehyde product can be separated in a washer (absorber), or by indirect cooling, or also by fractional cooling. For example, the washing may be performed with water in a multi-stage washer. An aqueous formaldehyde solution is thus obtained. From this solution, commercial formaldehyde can be collected by distillation, or other methods well known to those of ordinary skill, for immediate technical use. Alternatively, the formaldehyde may be condensed out of the exiting gases. In this manner, concentrated formaldehyde solutions may be obtained. Other ways for isolating and recovering the formaldehyde product are known to those of ordinary skill.

The principal undesirable product that is formed during the partial oxidation of methanol to formaldehyde is carbon monoxide, which may be accompanied by a small amount of carbon dioxide. Oxidation of the constituents of pulp mill or other waste gas streams can produce carbon oxides, sulfur oxides and possibly additional formaldehyde. Carbonyl sulfide (COS) may also be a minor product.

The residual gas stream, following removal of formaldehyde, may be treated in an incinerator, before discharging it into, for example, the ambient atmosphere. Alternatively, if the exiting gas contains a significant amount of residual methanol, the gas stream can be recycled for additional treatment in the catalytic reactor.

EXAMPLES

The invention will be further described by reference to the following examples. These examples are not intended to be construed in any way as limiting the scope of the invention. All patents, publications and any other references cited in this application are incorporated herein by reference in their entirety, respectively. In that regard, related provisional applications (1) "Vanadia-Titania//Metal-Molybdate Dual Catalyst Bed System and Process Using the Same for Methanol Oxidation to Formaldehyde" designated by Ser, No. 60/232,511 filed on even date and (2) "Metal Molybdate/Iron-Molybdate Dual Catalyst Bed System and Process Using the Same for Methanol Oxidation to Formaldehyde" designated Ser. No. 60/232,628 filed on even date are incorporated herein by reference in their entirety.

Example 1

The oxidation of methanol over the Engelhard catalysts was examined in a fixed-bed reactor. The Englehard catalysts comprised inert ceramic rings (e.g., 0–24" inert ceramic rings from Perstorp Polyols, Inc. of Todedo, Ohio) having thereon vanadia-titania (being used in the upstream region of the catalyst bed) and having thereon molybdena-titania (being used in the downstream region of the catalyst bed). Further, the weight percentages of the components for these catalysts were as follows: UPSTREAM REGION— 90% by weight inert ceramic ring and 10% by weight vanadia-titania of which 1% by weight (i.e., 1% of the 10%) was vanadia and 99% by weight (i.e., 99% of the 10%) was titania; and DOWNSTREAM REGION—90% by weight inert ceramic ring and 10% by weight molybdena-titania of which 1% by weight (i.e., 1% of the 10%) was molybdena and 99% by weight (i.e., 99% of the 10%) was titania. Unless indicated otherwise, these weight percentages were based on the total weight of the catalyst including the weight of any inert material.

The titania component was obtained from Bayer Corporation. The titania component of these catalysts had a surface area of 100 m$^2$/gm prior to calcination. The titania component was calcined without the vanadia or the molybdena component of the catalyst. After calcination between 600° C.–800° C., the titania component had a surface area was from 10–15 m$^2$/gm, preferably 10 m$^2$/gm. The calcined titania was used to form the desired vanadia-titania and the molybdena-titania catalysts having the above-indicated weight percentages. The vanadia-titania and molybdena-titania were supplied by Engelhard Corp having the above-identified weight percentages for the vanadia, molybdena, titania and inert material.

Each catalytic test consisted of nine catalyst pellets with a gas stream of $CH_3OH/O_2$/He (having a molar ratio of $CH_3OH/O_2$/He of 6/16/78) at a total flow rate of 100 sccm. A mixture of helium and oxygen from two mass flow controllers (Brooks) were bubbled through a methanol saturator cooled by flowing water from a cooler (Neslab RTE 110) to obtain a 6/16/78 ($CH_3OH/O_2$/He mole %; totaling 100 mole %) mixture of methanol/oxygen/helium and a flow rate of ~100 standard cubic centimeter per minute (sccm). The reactor was held vertical and made of a suitable outer diameter (e.g., >6-mm, adjusted as necessary to hold the volume and weight of the catalyst(s) being used in the upstream and downstream region of the catalyst bed) Pyrex glass. The catalysts (vanadia-titania in the upstream region and molybdena-titania in the downstream region) were held at the middle of the Pyrex tube (e.g., along the longitudinal length). The outlet of the reactor to the gas chromatograph (GC) was heated at 393–403° K (or as necessary) in order to avoid condensation of the products. The products were analyzed by a GC (HP5840) equipped with two TCDs (Thermal Conductive Detector) and a FID (Flame Ionization Detector), and two columns (Poropak R and Carbosieve SII) connected in parallel. Blank runs were performed on the Pyrex tube packed with quartz wool without any detectable conversions.

In order to examine the full effect of temperature on methanol oxidation, the reactor temperature was varied from about 200° C. to about 400° C. The reaction products were analyzed with the above-identified gas chromatograph. See, for example, G. Deo and I. Wachs, *J. Catal.* 146, 323–334 (1994); and G. Deo and I. Wachs, *J. Catal.* 146, 335–345 (1994).

The test results for catalyst (a) of $MoO_3/TiO_2$ alone, catalyst (b) of $V_2O_5/TiO_2$ alone, and combination catalyst (c) of $V_2O_5/TiO_2$ followed by $MoO_3/TiO_2$ (with a vanadia-titania/molybdena-titania depth ratio of 1:2; specifically, 3 pellets of $V_2O_5/TiO_2$ at the entrance (upstream) region and 6 pellets of $MoO_3/TiO_2$ in the middle and exit (downstream) regions of the reactor) are presented in Table 1 below.

Catalyst (a) of $MoO_3/TiO_2$ alone yielded a conversion of approximately 99% and a formaldehyde selectivity of 88% at 390° C. However, with prolonged use, catalyst (a) is prone to the volatility problems associated with $MoO_3$ as previously explained in detail. Catalyst (b) of $V_2O_5/TiO_2$ catalyst alone yielded a conversion of approximately 99% and a formaldehyde selectivity of approximately 25% at 340° C. Combination catalyst (c) in the small laboratory reactor yielded about a 99% conversion and a selectivity (formaldehyde) of 72% at 360° C.

TABLE 1

Methanol Conversion and Product Selectivity

| Catalyst | T (° C.) of catalyst | Conversion (%) | HCHO | DME | MF | DMM | CO | CO$_2$ |
|---|---|---|---|---|---|---|---|---|
| (a) | 260 | 15.1 | 72.9 | 16.0 | — | 11.1 | — | — |
| MoO$_3$/ | 340 | 89.7 | 87.8 | 5.0 | 1.0 | 0.4 | 5.8 | — |
| TiO$_2$ | 390 | 98.8 | 88.1 | 1.8 | — | — | 9.7 | 0.4 |
| (b) | 230 | 10.2 | 90.0 | — | — | 10.0 | — | — |
| V$_2$O$_5$/ | 285 | 70.5 | 70.5 | 1.3 | 6.5 | 0.6 | 21.1 | — |
| TiO$_2$ | 340 | 99.3 | 25.2 | 0.8 | — | — | 74.0 | — |
| (c) | 250 | 14.7 | 88.0 | 3.5 | — | 8.5 | — | — |
| (b)//(a) | 300 | 68.6 | 87.0 | 4.3 | 2.2 | 4.7 | 1.8 | — |
|  | 360 | 99.2 | 72.3 | 1.0 | — | — | 26.7 | — |

According to Table 1, supported MoO$_3$ catalysts (e.g., MoO$_3$ supported on TiO$_2$) do not significantly oxidize formaldehyde to carbon monoxide over the useful temperature range. Therefore, according to the invention, these supported MoO$_3$ catalysts were used as finishing catalysts (catalyst in the exit or downstream region) in methanol oxidation fixed-bed reactors. Supported $V_2O_5$ (e.g., $V_2O_5$ supported by $TiO_2$) catalysts are very active and selective at low methanol conversions, but tend to decompose formaldehyde into carbon monoxide at higher methanol conversions. Thus, according to the invention, supported $V_2O_5$ catalysts were used as starting catalysts (catalysts in the entrance or upstream region) in methanol oxidation reactors. In accordance with this invention, the selectivity of the dual catalysts (catalyst (c) where the upstream region contains catalyst (b) and the downstream region contains catalyst (a)) yielded substantially higher conversion m combination with high formaldehyde selectivity between 250° C. and 350° C. Accordingly, it is expected that a larger and/or longer commercial-size reactor which eliminates and/or substantially reduces back-mixing and non-plug flow (i.e., see definition of plug-flow in *Chemical Engineer's Handbook*, Robert H. Perry and Cecil H. Chilton, 5th Ed., pg. 4–22, McGrawHill, 1973) behavior associated with the exemplary smaller reactor of example 1 will yield improved conversions and (formaldehyde) selectivities.

Example 2

The oxidation of methanol over the Engelhard catalysts was examined in a fixed-bed reactor. The fixed bed reactor comprises:

1. Liquid methanol storage, metering and vaporization equipment.
2. "SOG" (Stripper Overhead Gas) delivery and metering equipment.
3. Process gas compression and metering equipment.
4. A reactor unit comprised of:
   a. A one inch OD, 60 inch long, 14 BWG, carbon steel tube surrounded by:
      1) A circulating, temperature controlled, bath of a heat transfer oil with an atmospheric boiling point of 257° C.
      2) A vapor pressure measurement and control system for the heat transfer oil.
      3) A stainless steel tube thermowell of diameter of 0.125 inch extending axially for the length of the tube, containing a wire thermocouple capable of being positioned at any point within the length of the thermowell.
5. A catalyst bed installed in the reactor tube void space of 0.834 inch diameter, which may vary in depth from essentially zero inch to 48 inches and may be comprised of one or more subdivisions of catalyst types, mixtures, or inert materials.
6. Formaldehyde separation equipment commonly known as an "Absorber" comprised of four sections of packing and the required handling equipment for circulation and cooling.
7. Piping and equipment necessary for operation of the catalyst bed in a recycle mode so as to allow the oxygen level of the process gas to be controlled at less than atmospheric levels.
8. Oxygen measuring and control equipment for maintaining precise control of oxygen in the catalyst bed.
9. Instrumentation and equipment to control the process gas pressure during the formaldehyde manufacturing process.

Each catalytic test consisted of the upstream fourth of the catalyst bed filled with vanadia-titania catalyst on a ceramic support and the downstream three-fourths of the catalyst bed filled with molybdena-titania catalyst on a ceramic support. The total gas flow had a space velocity ranging from 0.82/sec to 2.61/sec. Space velocity is measured in $sec^{-1}$. Space velocity equals (((sccm of gas flow)/(cc of catalyst volume))×((1 min)/(60 sec))). Both pure methanol streams and streams where 20% of the methanol came from stripper overhead gas (SOG—a waste gas stream from a pulp mill) were examined. To the pulp mill waste gas stream, MeOH and air were added to yield e.g., 6%–10% MeOH/10%–20% $O_2$/80%–84% $N_2$. The reactor temperature was varied from about 305° C. to about 330° C. (as indicated in Table 2 below) in order to examine the full effect of time and temperature on catalytic methanol oxidation. The inlet and outlet gas stream components were determined using a gas chromatograph. The reaction products were analyzed with a gas chromatograph: MTI Q30H with one 14 meter OV-1 column, one 8 meter Stabilwax column and one 10 meter Molsieve SA column obtained from Union Carbide of Danbury, Conn. The test results are provided in Table 2 below.

TABLE 2

Effect of Velocity and Temperature on Conversion and Selectivity

Pure Methanol Streams

| Space Velocity ($sec^{-1}$) | Temp (° C.) | Conversion (%) | Selectivity (%) | Approximate Oxygen (%) |
|---|---|---|---|---|
| 0.82 | 330 | 98.3 | 76.6 | 19 |
| 0.82 | 327 | 96.7 | 81.6 | 19 |
| 0.82 | 325 | 93.8 | 82.4 | 19 |
| 0.82 | 320 | 89.2 | 83.2 | 19 |
| 0.82 | 320 | 85.1 | 81.2 | 20 |
| 0.82 | 315 | 79.6 | 84.3 | 19 |
| 0.82 | 310 | 68.4 | 83.8 | 19 |
| 0.82 | 305 | 59.8 | 81.2 | 19 |
| 1.12 | 327 | 90.5 | 86.7 | 20 |
| 1.12 | 320 | 91.6 | 85.2 | 17 |
| 1.12 | 326 | 87.4 | 83.3 | 10 |
| 1.49 | 320 | 87.6 | 87.0 | 20 |
| 1.87 | 320 | 81.7 | 88.5 | 20 |
| 1.87 | 320 | 81.5 | 88.1 | 20 |
| 2.24 | 320 | 72.0 | 87.8 | 20 |
| 2.24 | 325 | 73.2 | 89.5 | 19 |
| 2.61 | 320 | 70.2 | 88.6 | 20 |

Methanol with 20% SOG

| Space Velocity ($sec^{-1}$) | Temp (° C.) | Conversion (%) | Selectivity (%) | Oxygen (%) |
|---|---|---|---|---|
| 0.82 | 327 | 14.9 | 42.3 | 19 |
| 0.82 | 324 | 11.9 | 68.1 | 18 |
| 1.12 | 326 | 13.9 | 80.8 | 17 |
| 1.12 | 325 | 6.6 | 66.8 | 17 |
| 1.28 | 320 | 3.0 | 84.7 | 10 |
| 2.24 | 321 | 3.8 | 19.3 | 19 |
| 2.24 | 319 | 6.7 | 90.3 | 20 |

Example 3

The same fixed-bed reactor as in Example 2 above was used except that before the inlet end of the reactor, a carbon trap of 3 ¼ inches internal diameter by 10 inches length (to provide an exemplary residence time of 3 seconds) was inserted. The carbon trap filled with Sorbonorit B4 950460 carbon cylinders of ⅛ inch diameter by 7/16 inch length obtained from Norit Nev., PO Box 105, 3800 AC Amersfoort, The Netherlands was used. Catalyst rings of 3/16 inch outer diameter and 1/16 inch internal diameter and 7/32 inch length were also used between the carbon trap and the inlet end of the fixed bed reactor. Use of the aforementioned carbon trap containing the Sorbonorit B4 950460 carbon cylinders yielded a formaldehyde yield (yield=conversion× selectivity) of 60.27%, 59.41% and 61.51% at 325° C. The carbon traps are believed to be useful for the removal of VOCs (e.g., terpenes) from a waste gas stream from a pulp mill before the pulp mill waste gas stream is fed into the inlet end of the fixed bed reactor.

What is claimed is:

1. A catalyst bed having a total bed depth, a length, an upstream region, a downstream region and an outlet, said catalyst bed comprising:
    (a) a vanadia-titania catalyst in said upstream region wherein said vanadia-titania catalyst is substantially free of $MoO_3$; and
    (b) a molybdena-titania catalyst in said downstream region wherein said molybdena-titania catalyst initially is free or substantially free of $V_2O_5$.

2. The catalyst bed according to claim 1, wherein said upstream region is from about a first fourth to about a first half of said depth nearest said inlet and said downstream region is from about three-fourths to about one-half of said depth nearest said outlet.

3. The catalyst bed according to claim 1, wherein said upstream region is from about a first third to about a first half of said depth nearest said inlet and said downstream region is from about two-thirds to about one-half of said depth nearest said outlet.

4. The catalyst bed according to claim 1, wherein said upstream region is about a first third of said depth nearest said inlet and said downstream region is about two-thirds of said depth nearest said outlet.

5. The catalyst bed according to claim 1, wherein a depth ratio of said upstream region to said downstream region is about 1:2.

* * * * *